(12) United States Patent
Caldwell

(10) Patent No.: US 7,122,819 B2
(45) Date of Patent: Oct. 17, 2006

(54) METHOD AND APPARATUS FOR IMAGER DIE PACKAGE QUALITY TESTING

(75) Inventor: John L. Caldwell, Meridian, ID (US)

(73) Assignee: Micron Technology, Inc., Boise, ID (US)

( * ) Notice: Subject to any disclaimer, the term of this patent is extended or adjusted under 35 U.S.C. 154(b) by 229 days.

(21) Appl. No.: 10/839,356

(22) Filed: May 6, 2004

(65) Prior Publication Data
US 2005/0247896 A1 Nov. 10, 2005

(51) Int. Cl.
*G01N 21/88* (2006.01)
*G01N 21/00* (2006.01)
*G06K 9/00* (2006.01)

(52) U.S. Cl. .................. 250/559.45; 382/141; 382/145; 356/237.1; 356/239.2

(58) Field of Classification Search ........... 250/559.12, 250/559.45; 382/141, 145, 147; 356/237.1, 356/239.2
See application file for complete search history.

(56) References Cited

U.S. PATENT DOCUMENTS

| | | | |
|---|---|---|---|
| 4,815,844 A * | 3/1989 | Schmalfuss et al. ..... | 356/239.7 |
| 5,459,932 A * | 10/1995 | Rando et al. ................. | 33/291 |
| 6,140,630 A | 10/2000 | Rhodes | |
| 6,204,524 B1 | 3/2001 | Rhodes et al. .............. | 382/154 |
| 6,205,243 B1 * | 3/2001 | Migdal et al. .............. | 382/154 |
| 6,310,366 B1 | 10/2001 | Rhodes et al. | |
| 6,326,652 B1 | 12/2001 | Rhodes | |
| 6,333,205 B1 | 12/2001 | Rhodes | |
| 6,376,868 B1 | 4/2002 | Rhodes | |
| 6,465,801 B1 * | 10/2002 | Gann et al. .............. | 250/559.4 |
| 6,734,997 B1 * | 5/2004 | Lin ........................... | 358/487 |
| 6,795,175 B1 * | 9/2004 | Hunt ....................... | 356/237.2 |
| 2001/0015414 A1 * | 8/2001 | Keranen et al. ....... | 250/559.45 |
| 2004/0037457 A1 * | 2/2004 | Wengender et al. ........ | 382/141 |
| 2005/0116187 A1 * | 6/2005 | Uda et al. .............. | 250/559.45 |

* cited by examiner

*Primary Examiner*—Georgia Epps
*Assistant Examiner*—Brian Livedalen
(74) *Attorney, Agent, or Firm*—Dickstein Shapiro LLP

(57) ABSTRACT

An apparatus and method of detecting a defect in an imager die package. The method comprises the steps of exposing the imager die package to light at a first angle, exposing the imager die package to light at a second angle, outputting electrical signals based on the exposures; and determining the level at which a defect is present based on the output electrical signals. An exemplary embodiment of the apparatus comprises a first light source positioned over an imager die package at a first angle, a second light source over the imager die package at a second angle, said first and second angles being different from each other; and a processor for determining a level of defection in the die package.

50 Claims, 15 Drawing Sheets

METHOD AND APPARATUS FOR IMAGER DIE PACKAGE QUALITY TESTING

FIELD OF THE INVENTION

The present invention relates to a method and apparatus for imager die package quality testing.

BACKGROUND OF THE INVENTION

Integrated circuits, including dies, for example, imager dies such as charge-coupled-devices (CCD) and complementary metal oxide semiconductor (CMOS) dies, have commonly been used in photo-imaging applications.

Imager dies, such as the CMOS imager die, typically contain thousands of pixels in a pixel array to be used in a single chip. Pixels convert light into an electrical signal that can then be stored and recalled by an electrical device such as, for example, a processor. The electrical signals that are stored may be recalled to produce an image on, for example, a computer screen.

Exemplary CMOS imaging circuits, processing steps thereof, and detailed descriptions of the functions of various CMOS elements of an imaging circuit are described, for example, in U.S. Pat. No. 6,140,630, U.S. Pat. No. 6,376,868, U.S. Pat. No. 6,310,366, U.S. Pat. No. 6,326,652, U.S. Pat. No. 6,204,524, and U.S. Pat. No. 6,333,205, all of which are assigned to Micron Technology, Inc. The disclosures of each of the forgoing patents are hereby incorporated by reference in their entirety.

FIG. 1 illustrates a block diagram of an imager die 110 having a CMOS imager device 108 formed therein. The CMOS imager device 108 has a pixel array 114 that comprises a plurality of pixels arranged in a predetermined number of columns and rows. The pixel cells of each row in pixel array 114 are all turned on at the same time by a row select line (not shown), and the pixel cells of each column are selectively output by respective column select lines (not shown). A plurality of row and column lines are provided for the entire pixel array 114. The row lines are selectively activated in sequence by a row driver 101 in response to a row address decoder 102. The column select lines are selectively activated in sequence for each row activation by a column driver 103 in response to a column address decoder 104. The CMOS imager device 108 is operated by a control circuit 105, which controls the address decoders 102, 104 for selecting the appropriate row and column lines for pixel readout, and row and column driver circuitry 101, 103 to apply driving voltage to the drive transistors of the selected row and column lines.

Output signals typically include a pixel reset signal $V_{rst}$, taken from a charge storage node after the pixel is reset, and a pixel image signal $V_{sig}$, which is taken from the charge storage node after charges generated by an image are transferred to the node. The $V_{rst}$ and $V_{sig}$ signals are read by a sample and hold circuit 106 and are subtracted by a differential amplifier 107, which produces a difference signal ($V_{rst}$–$V_{sig}$) for each pixel cell that represents the amount of light impinging on the pixels. This difference signal is digitized by an analog-to-digital converter 109. The digitized difference signals are then fed to an image processor 111 to form and output a digital image. In addition, as depicted in FIG. 1, the imager die 110, and, thus, CMOS imager device 108, may be included on a single semiconductor chip.

Imager dies, e.g., imager die 110, are typically packaged and inserted into imaging devices such as, for example, a digital camera. FIG. 2 illustrates a cross-sectional view of one conventional imager die package 100. The illustrated package 100 includes the imager die 110 positioned on a substrate 112. As discussed above, the imager die 110 has an imager device 108 (FIG. 1) having a pixel array 114 formed therein. In the package 100, the imager die 110 typically has a transparent element 116 over the pixel array 114. The transparent element 116 is typically attached to the imager die 110 by an adhesive material 118, or any other material that can support the transparent element 116 over the pixel array 114.

In operation, light radiation enters the transparent element 116 of the imager die package 100. The transparent element 116 filters out IR radiation that can cause color shifts in the pixel array 114. Light radiation is then adsorbed, and image signals are created by the pixel array 114, which converts the photons from light radiation to electrical signals, as discussed above with respect to FIG. 1. Wire bonds 122 conduct electrical output signals from the imager die 110 to wiring on the substrate 112, which, in turn, connects to external circuitry.

In displaying an acquired image, a display structure, for example, a computer screen, will display a complete image only if the complete image is captured by the pixel array 114. For example, if the pixel array 114 were subjected to white light from a light source 130 (FIG. 5), the expected display image would be an all white image. If the pixel array 114 is unable to capture the entire image, however, an incomplete display image 300, illustrated in FIG. 3, will be displayed on a computer screen. The illustrated display image 300 appears to have a completely white surface with a "hole" or defect 124 created by the failure to capture the complete image (in this case, a white light) from the pixel array 114. For the sake of clarity, only a portion of the full image having the defect 124 has been illustrated, and has been magnified for illustrative purposes.

The defect 124 may be a result of two separate and distinct causes. One possible reason for the defect 124 is that the pixel array contains one or more non-functional pixels (i.e., the array is defective). A top-down view of a section 400 of a pixel array having a defective pixel is illustrated in FIG. 4. The illustrated section 400 has a single non-functional pixel 126. The non-functional pixel 126 may receive light, but may not be able to convert the light into an electrical signal that can be stored and recalled as described above with respect to FIG. 1, resulting in a defect 124 (FIG. 3).

Imager die packages having non-functional pixels 126 will likely be segregated into groups by the manufacturer, depending on the number of non-functional pixels each package contains. These groups of packages, can be salvaged and used for various applications, or, if necessary, can be discarded completely. For example, the imager die package 100 (FIG. 1) having the non-functional pixel 126 could be used in applications that do not require the highest resolution, and would likely not be used in high-end applications such as, for example, professional photography equipment. Alternatively, the imager die package 100 could be discarded altogether if it contains a significant number of non-functional pixels.

A second reason for the image defect 124 (FIG. 3) may be related to particulate contamination of the transparent element 116 (FIG. 2). FIG. 5, for example, illustrates a particle 128 present on the transparent element 116. The particle 128 may have resulted from the fabrication processing of the imager die 110. During testing or operation of the imager die package 100, the particle 128 prevents light from the light source 130 from reaching the corresponding pixel (represented by the "X") of pixel array 114, resulting in the defect 124 illustrated in FIG. 3.

Unlike the imager die having a non-functional pixel 126 (FIG. 4), the imager die 110 of FIG. 5 is fully functional. The output of electrical signals by the fully functional pixel array will, nevertheless, result in a display image similar to the display image 300 illustrated in FIG. 3. Because the particle 128 causes the fully functional array to produce a defective output image, the fully functional pixel array will be segregated into the groups of dysfunctional arrays discussed above that may be salvaged and used in low-end applications, or discarded altogether. Discarding fully functional pixel arrays results in lower yield, and increases the overall costs of production.

Accordingly, there is a need and desire for a method and apparatus for testing the quality of an imager die package, and determining the level at which the defect is present.

BRIEF SUMMARY OF THE INVENTION

The invention relates to an apparatus and method of detecting a defect in an imager die package. An exemplary embodiment of the method comprises the steps of exposing the imager die package to light at a first angle, exposing the imager die package to light at a second angle, outputting electrical signals based on the exposures; and determining the level at which a defect is present based on the electrical signals. An exemplary embodiment of the apparatus comprises a first light source positioned over an imager die package at a first angle, a second light source over the imager die package at a second angle, said first and second angles being different from each other; and a means for determining a level of defects in the die package.

BRIEF DESCRIPTION OF THE DRAWINGS

The above-described features of the invention will be more clearly understood from the following detailed description, which is provided with reference to the accompanying drawings in which.

DETAILED DESCRIPTION OF THE INVENTION

In the following detailed description, reference is made to the accompanying drawings, which form a part hereof and show by way of illustration specific embodiments in which the invention may be practiced. These embodiments are described in sufficient detail to enable those skilled in the art to practice the invention, and it is to be understood that other embodiments may be utilized, and that structural, logical, and electrical changes may be made without departing from the spirit and scope of the present invention. The progression of processing steps described is exemplary of embodiments of the invention; however, the sequence of steps is not limited to that set forth herein and may be changed as is known in the art, with the exception of steps necessarily occurring in a certain order.

Figure 6:
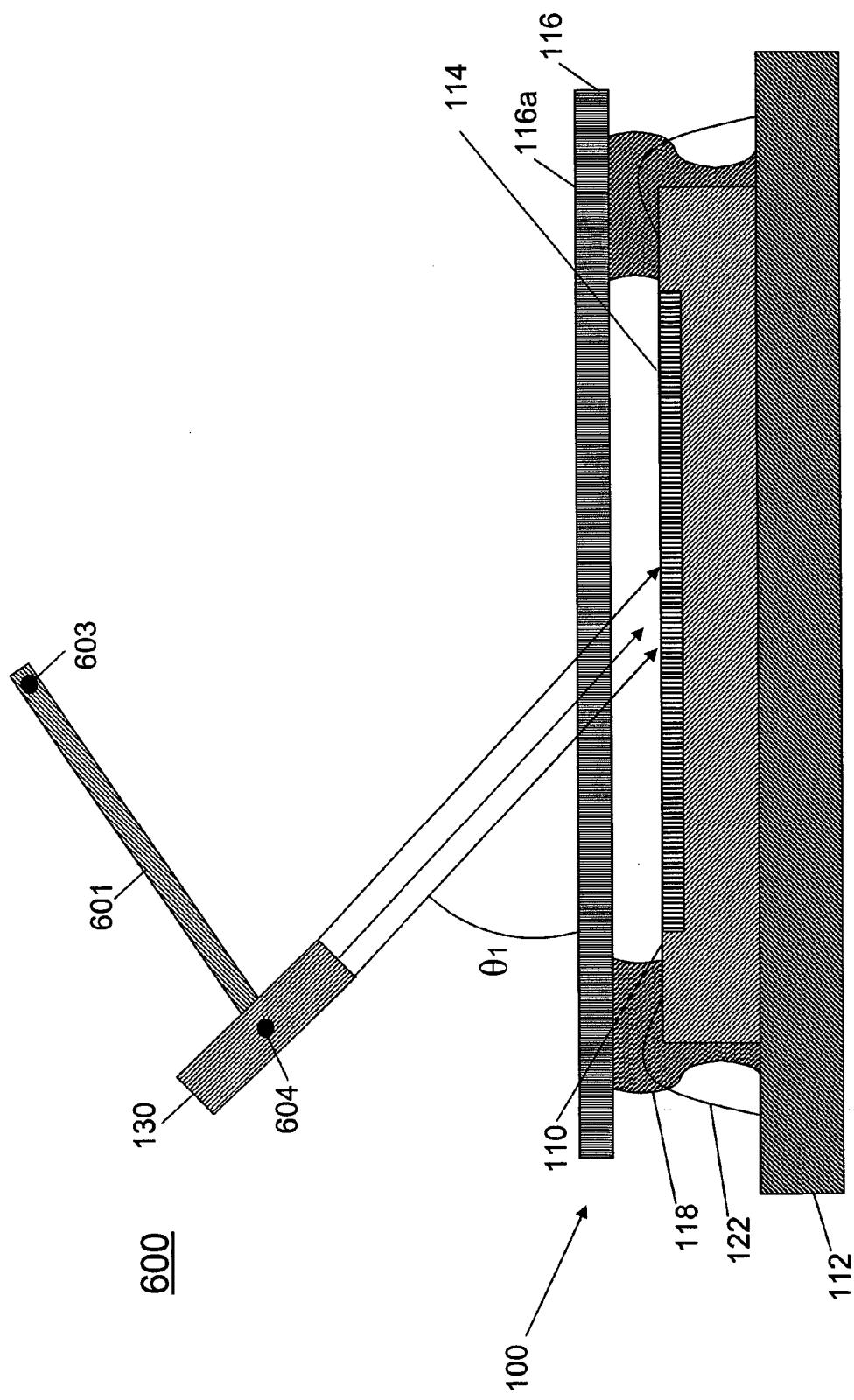
FIG. 6 illustrates an apparatus for testing the quality of an imager die package in accordance with a first exemplary embodiment of the invention.

Referring now to the drawings, where like reference numbers designate like elements, FIGS. 6–12 illustrate a first exemplary embodiment of an apparatus 600 designed to test the quality of an imager die package 100 and method of operation. The apparatus 600 includes a light source 130 suspended from a suspension structure 601 such that the light source 130 is rotatable and can move in relation to the imager die package 100. FIG. 6 illustrates the suspension structure 601 as rotatable around an axis 603. The apparatus is also illustrated as having the light source 130 rotatable around a second axis 604. By being rotatable, the light source 130 can emit light onto the imager die package 100, positioned underneath the light source 130, at various angles. The angles are measured in relation to a surface 116a of the transparent element 116. For example, FIG. 6 illustrates the light source 130 as emitting light onto the imager die package 100 at an angle represented by $\theta_1$. It should be noted that the light source 130 should be positioned at an angle of incidence such that the light does not simply reflect off the surface 116a of the transparent element 116, resulting in the failure by the pixel array 114 to capture an image.

In its operation, the imager die package 100 is positioned underneath the light source 130. The pixel array 114 of the imager die package 100 is exposed to light from the light source 130 at a first angle. The resulting image is stored, and the pixel array 114 is exposed to light from the light source 130 at a second angle. A second image is stored, and the first and second images can be displayed on, for example, a computer screen. The level at which the defect is present can be determined based on the display image, as discussed below in more detail.

Figure 1:
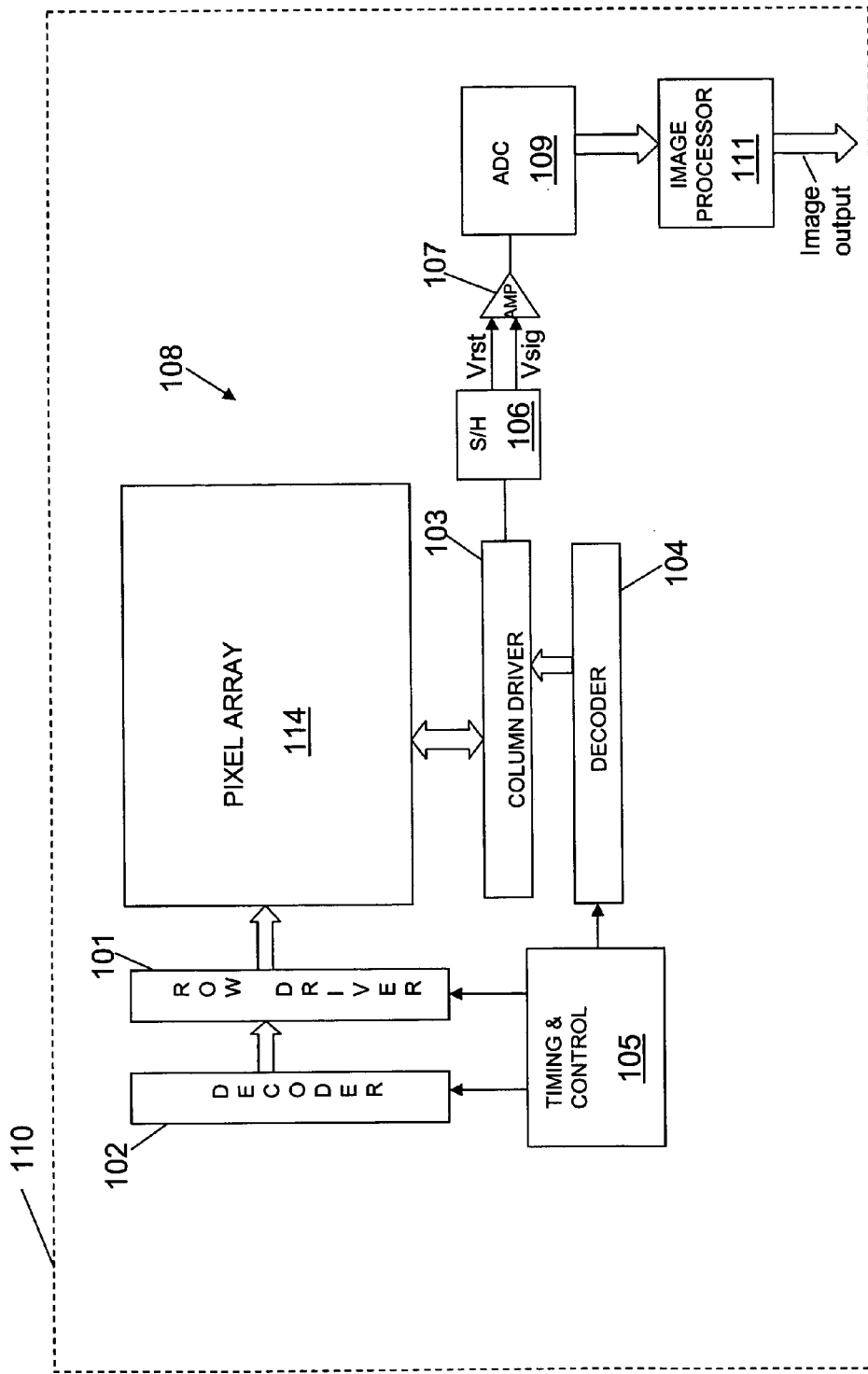
FIG. 1 is a block diagram of an imager die.
Figure 2:
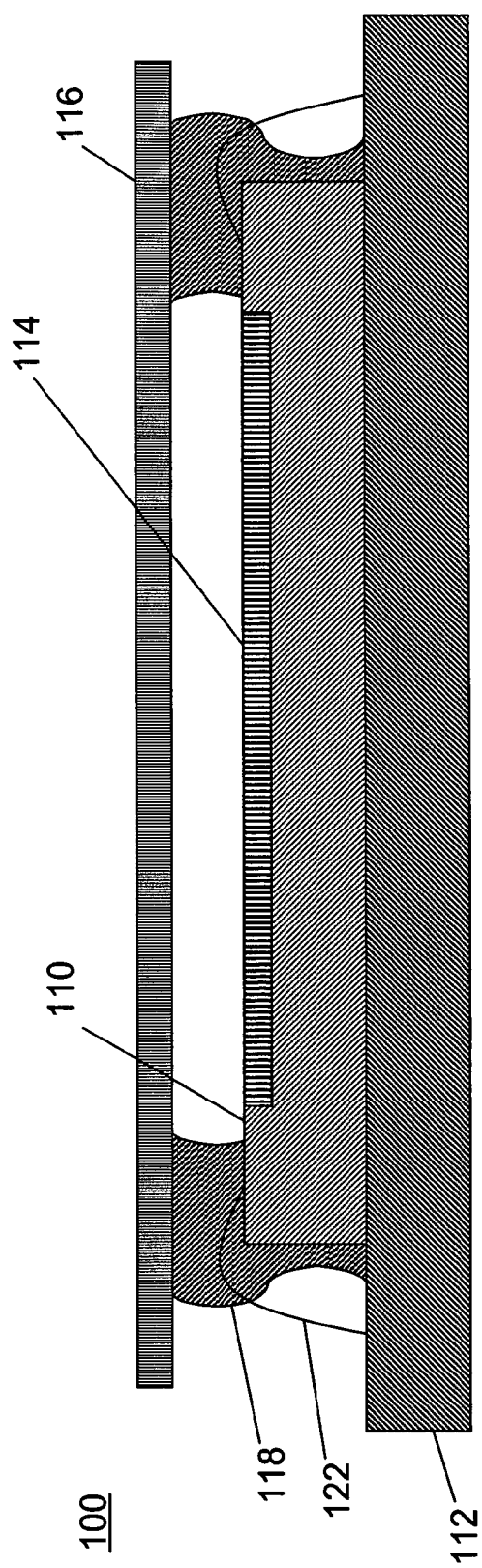
FIG. 2 illustrates a cross-sectional view of an imager die package.
Figure 7:
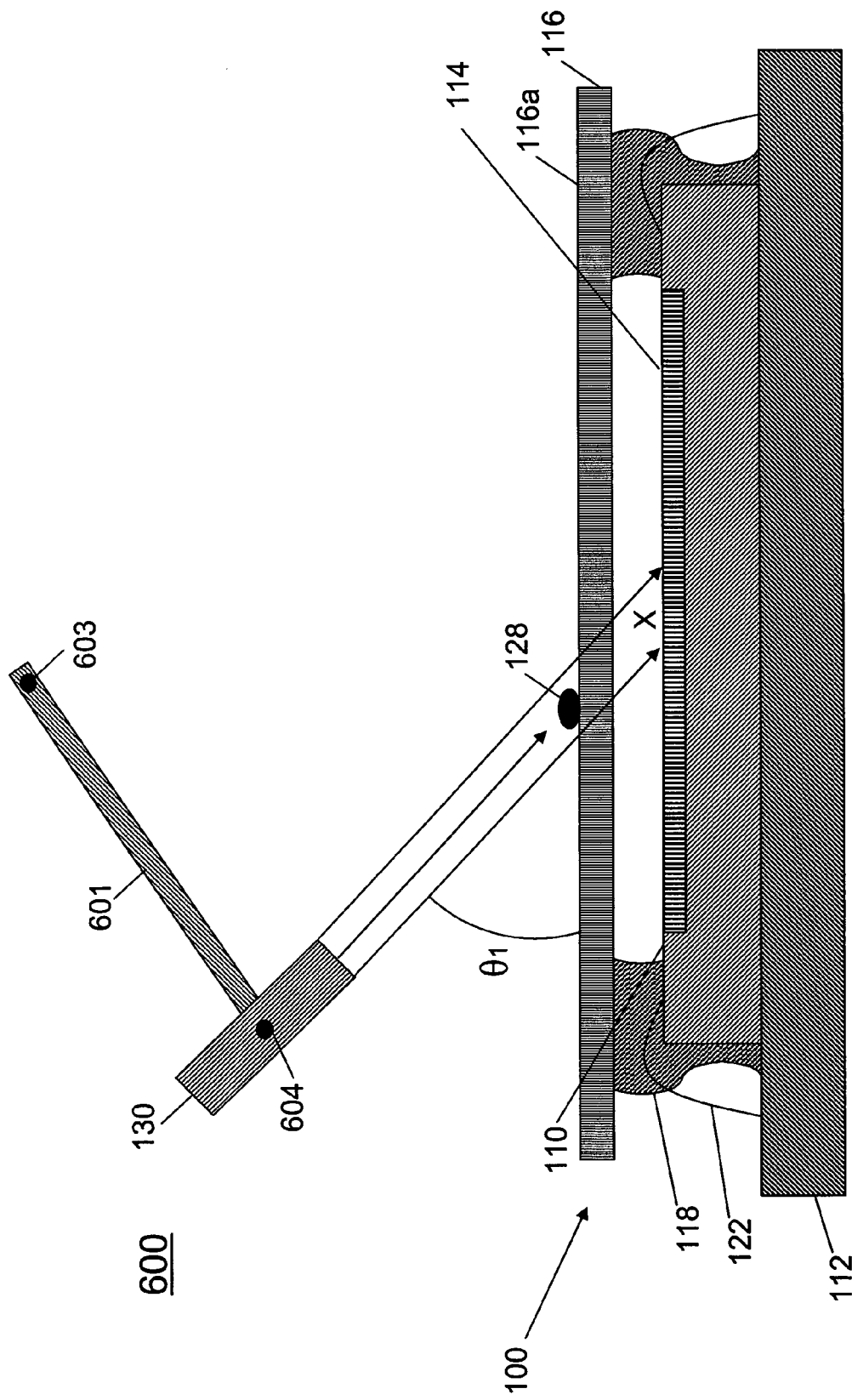
FIGS. 7 and 8 illustrate a first exemplary operation of the FIG. 6 apparatus.

FIG. 7 illustrates the FIG. 6 apparatus 600 as it operates on the imager die package 100. The pixel array 114 is exposed to light from the light source 130 at a first angle $\theta_1$. The light source 130 could be positioned over the imager die package 100 manually or automatically by, for example, a computer running a program. A particle 128 on the surface 116a of the transparent element 116 obstructs the path of the light emitted from the light source 130. The corresponding pixel (represented by the "X") fails to receive the light emitted from the light source 130, and, therefore, fails to convert the light into electrical signals. The other pixels of the pixel array 114 receive the light emitted from the light source 130, and convert the light into electrical signals that can be stored and later processed to form an image, as discussed above with respect to FIG. 1.

Figure 8:
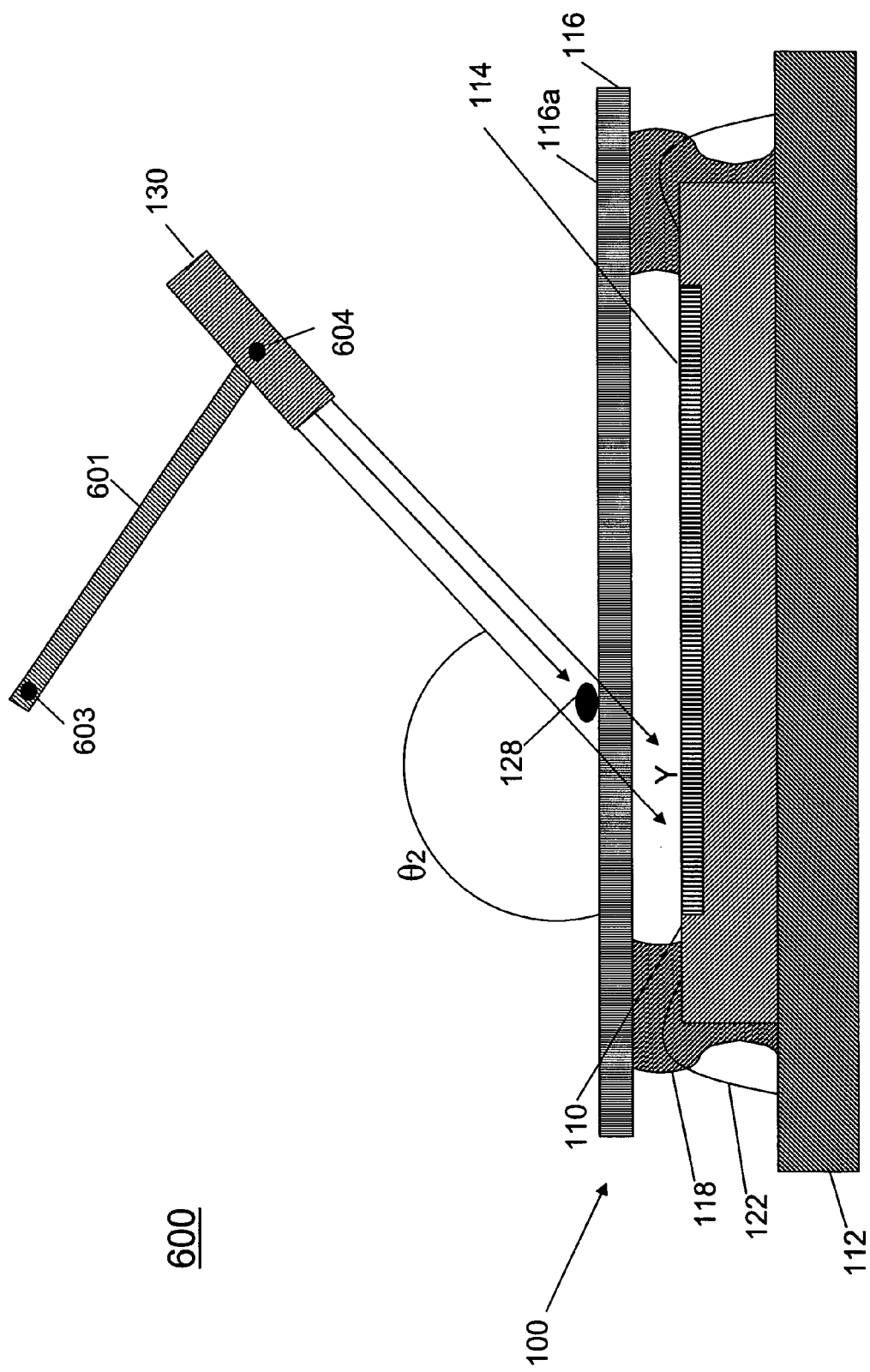

FIG. 8 illustrates the light source 130 moved to a different position, and rotated to emit light onto the pixel array 114 of the imager die package 100 at a second angle $\theta_2$. The second angle $\theta_2$ is different from the first angle $\theta_1$ (FIG. 7). As noted, the light source 130 could be moved either manually or automatically by, for example, a computer running a program. The particle 128 obstructs the light emitted from the light source 130, and the corresponding pixel (represented by the "Y") fails to receive the light emitted from the light source 130, and, therefore, fails to convert the light into electrical signals. The other pixels of the pixel array 114, including the pixel X that failed to receive light in FIG. 7, receive the light emitted from the light source 130, and convert the light into electrical signals that can be stored, and later processed to form an image.

Figure 9:
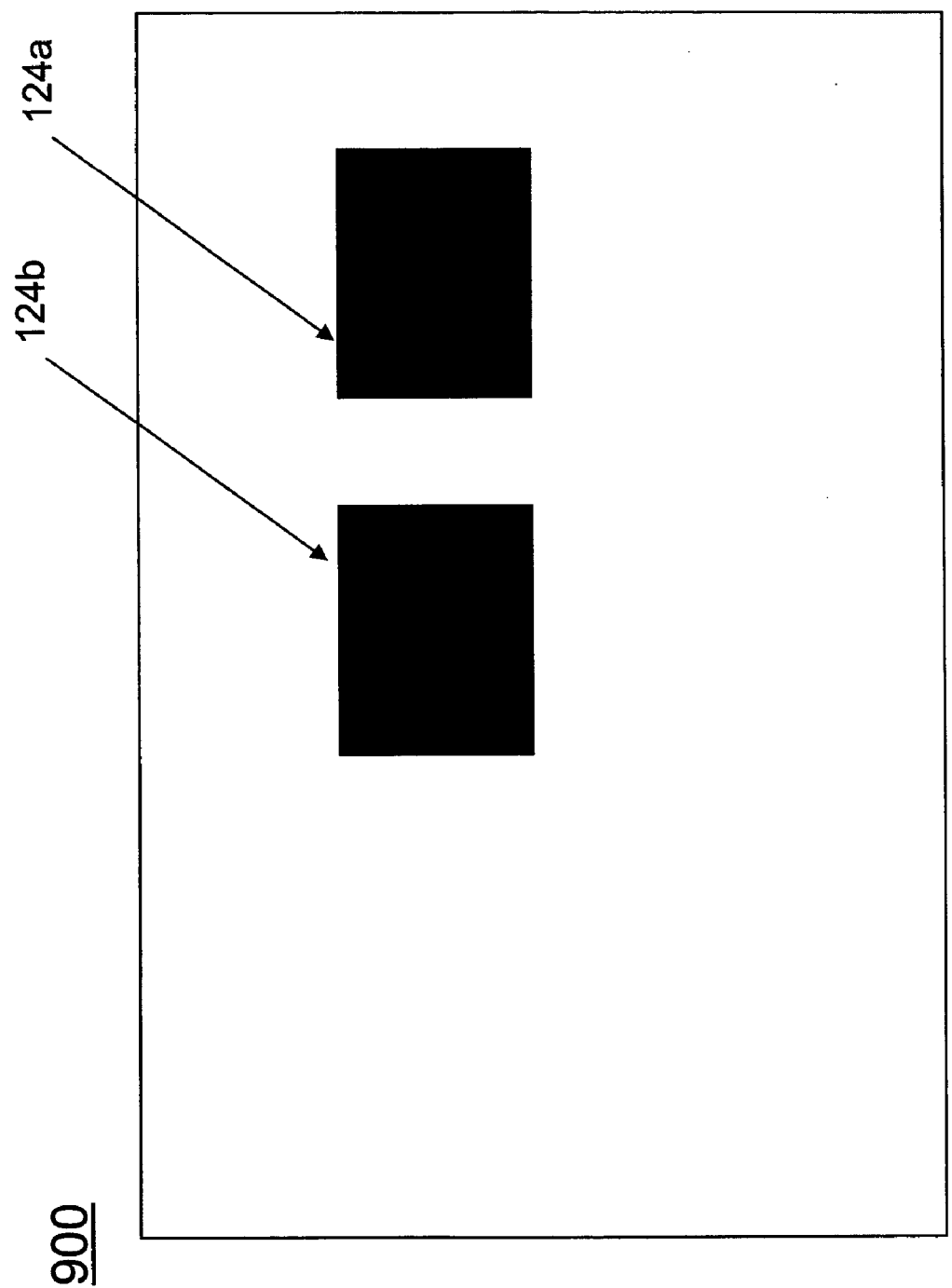
FIG. 9 illustrates a display image from the operation of the FIG. 6 apparatus in accordance with an exemplary embodiment of the invention.

The stored electrical signals are processed, as discussed above with respect to FIG. 1, to form a display image 900 illustrated in FIG. 9, which is a display of pixels receiving light from both exposures. The illustrated display image 900 shows two separate defects 124a, 124b resulting from the obstruction by the particle 128 (FIGS. 7 and 8) during the operation of the apparatus 600 (FIGS. 7 and 8). The two defects 124a, 124b correspond to the pixels X, Y (FIGS. 7 and 8) that could not receive or convert the light emitted from the light source 130. The two separate images could be compared by an operator, the image processor 111 (FIG. 1), or a processor-based system, and the determination can be made as to whether the defect lies in the transparent element 116 or the pixel array 114. In this case, the two defects 124a, 124b represent a defect at the transparent element 116 level as opposed to the pixel level that is detected by the present invention as discussed below with respect to FIGS. 10–12.

Figure 10:
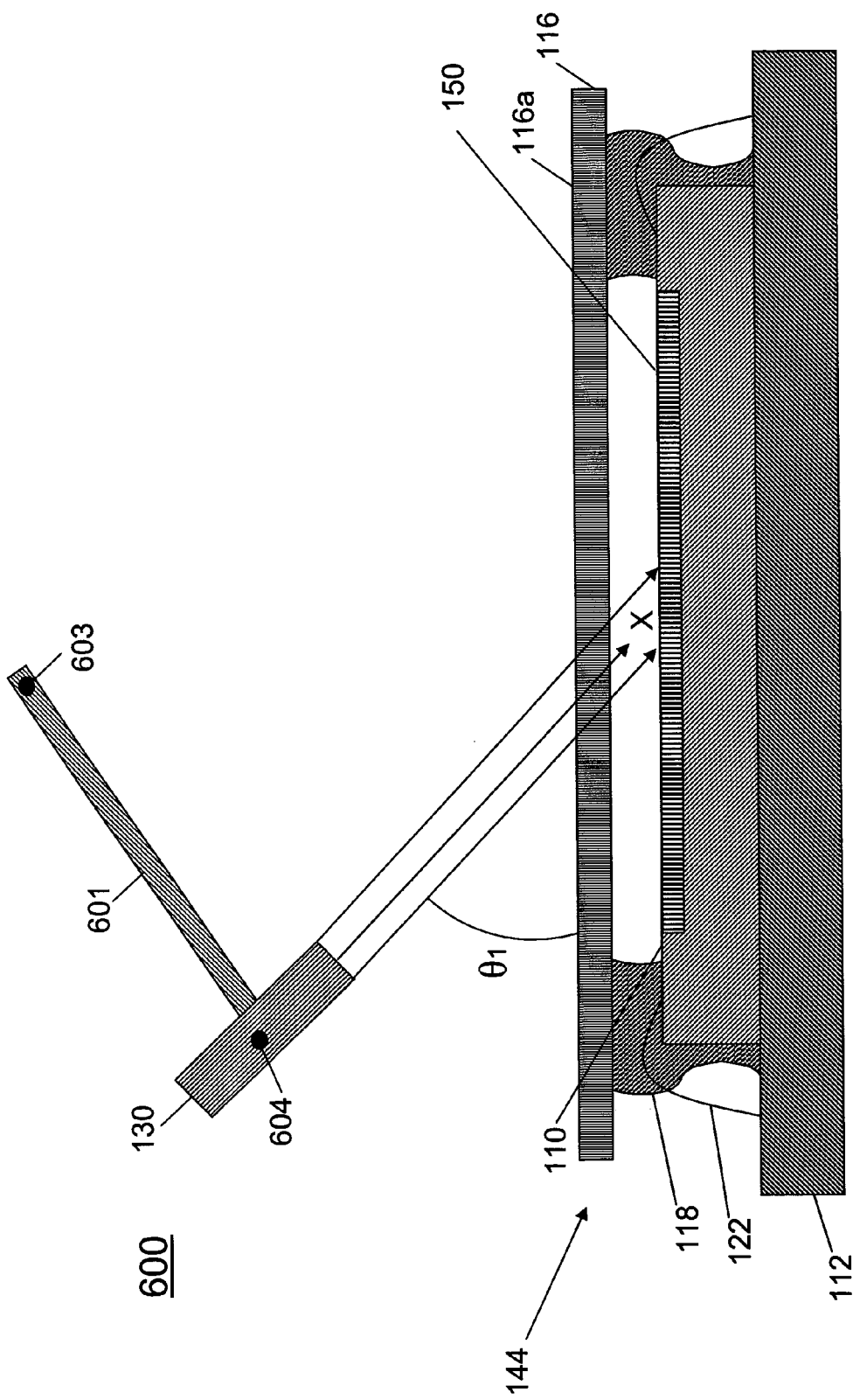
FIGS. 10 and 11 illustrate a second exemplary operation of the FIG. 6 apparatus.

FIG. 10 illustrates the apparatus 600 as it operates on an imager die package 144 having defective pixels. The defective imager die package 144 has a pixel array 150 containing a non-functional pixel, represented by X. The pixel array 150 of the imager die package 144 is exposed to light emitted from the light source 130 at a first angle $\theta_1$. The non-functional pixel X cannot convert the light emitted from the light source 130 to electrical signals for subsequent reading and processing. The other pixels in the pixel array, however, are operational, and convert the light into electrical signals. These signals are stored during operation.

Figure 11:
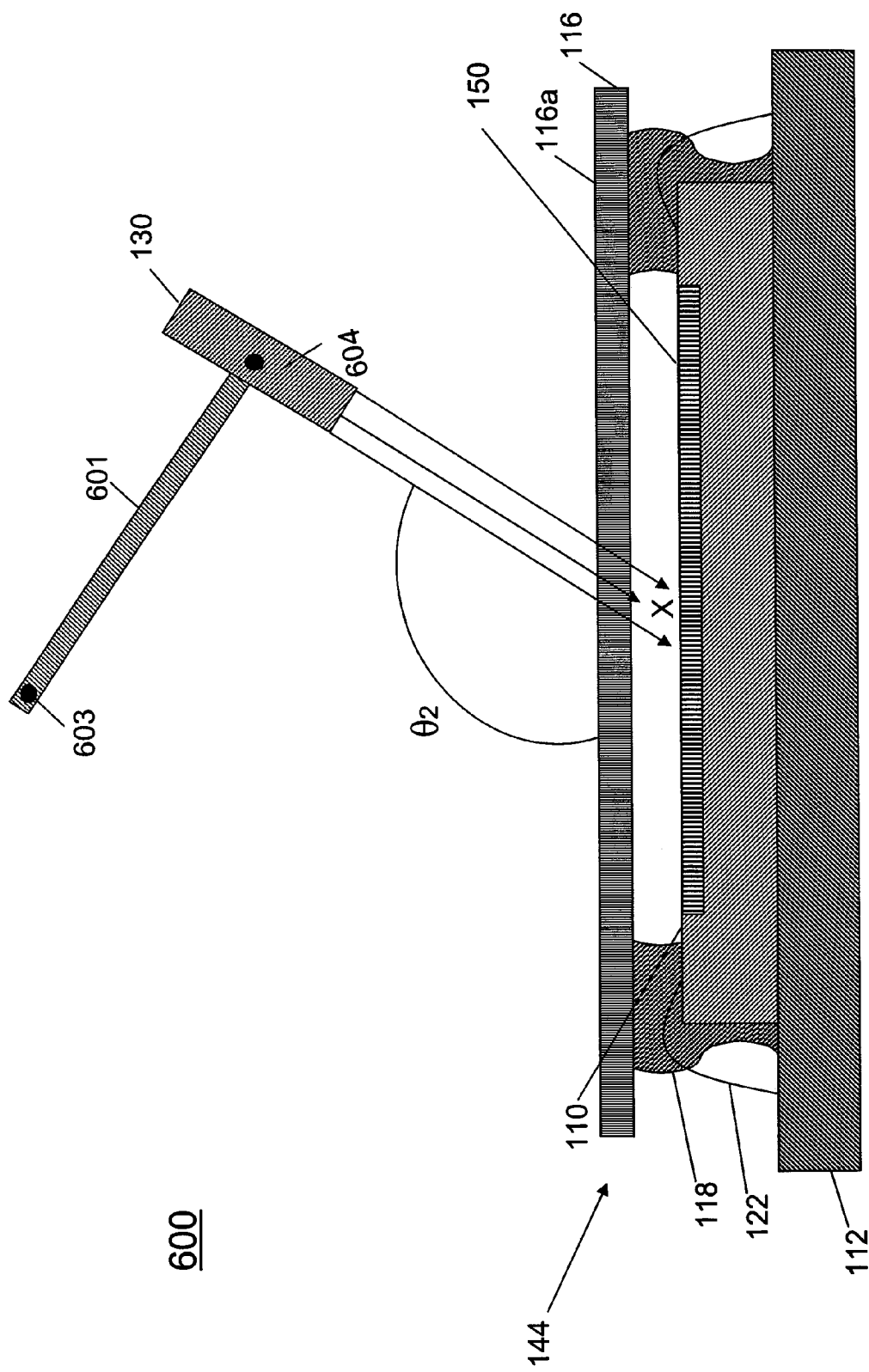

FIG. 11 illustrates the light source 130 at a different position, and, therefore, a second angle $\theta_2$. The pixel array 150 of the imager die package 144 is exposed to light emitted from the light source 130 at a second angle $\theta_2$. During its operation, non-functional pixel X cannot convert the light emitted from the light source 130 to electrical signals for subsequent reading and processing. The other pixels in the pixel array, however, are operational, and convert the light into electrical signals. These signals are stored during operation.

Figure 12:
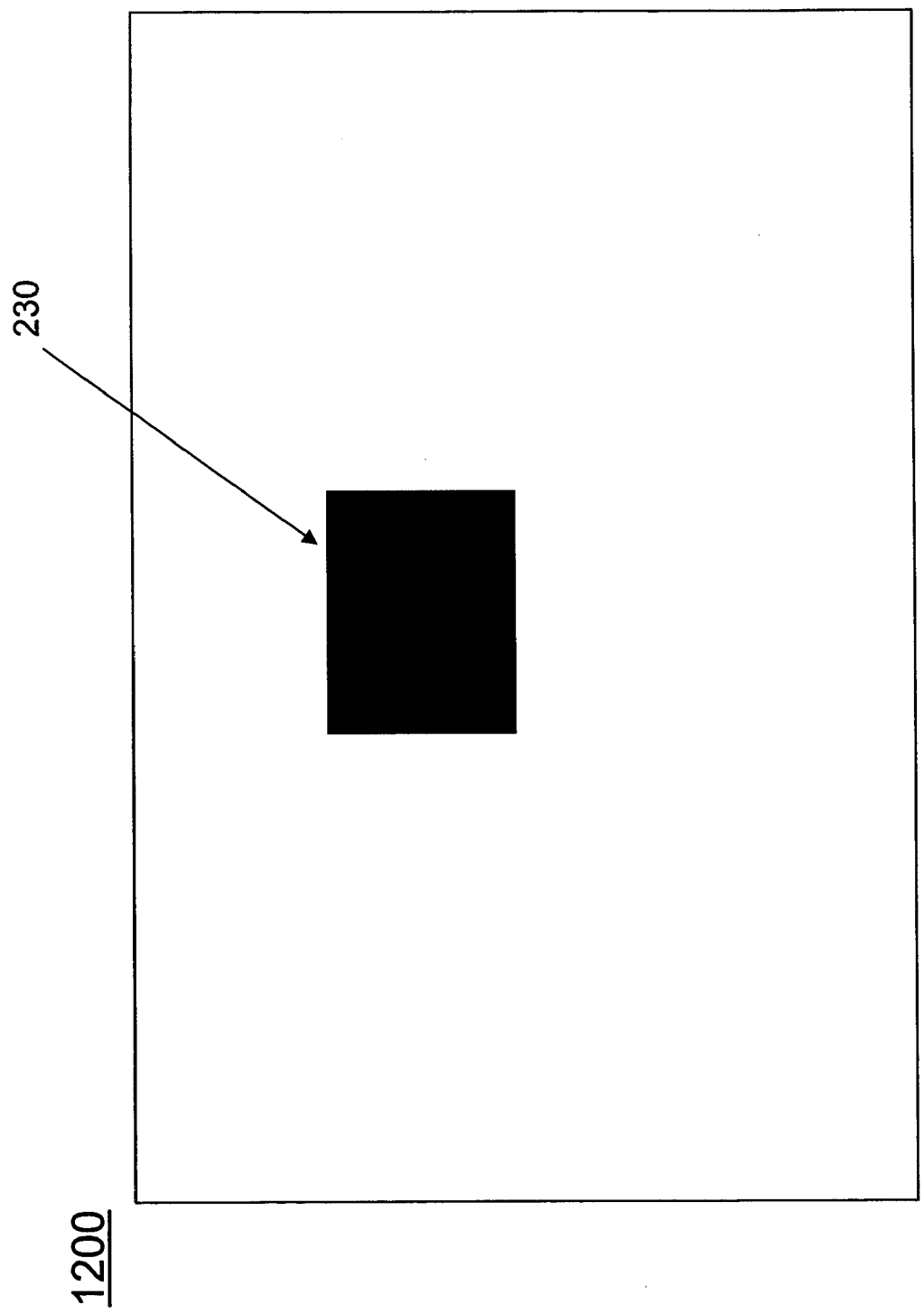
FIG. 12 illustrates a display image from the operation of the FIG. 6 apparatus in accordance with an exemplary embodiment of the invention.

The signals stored during operation are outputted as a display image 1200 illustrated in FIG. 12 which is a display of pixels receiving light from both exposures. The illustrated display image 1200 only has one defect 230. The reason for only one defect 230 is that regardless of the angle at which the light source 130 emits light, the non-functional pixel X (FIGS. 10 and 11) will not convert the light into electrical signals. In FIGS. 7–9, on the other hand, the pixel upon which the shadow from the particle 128 is cast is dependent upon the angle at which the light source 130 emits light.

Figure 4:
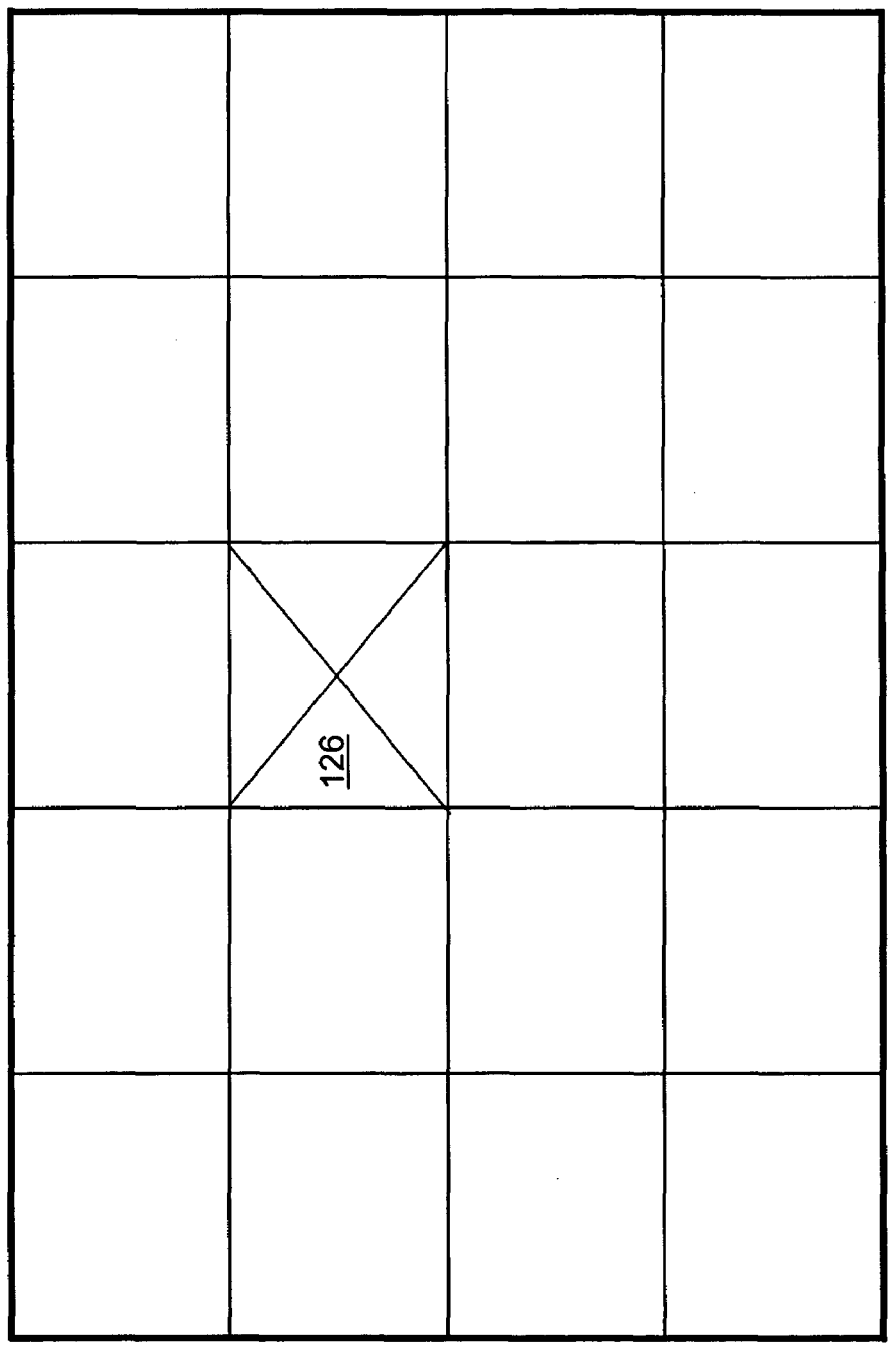
FIG. 4 illustrates a top-down view of a section of a defective pixel array.
Figure 5:
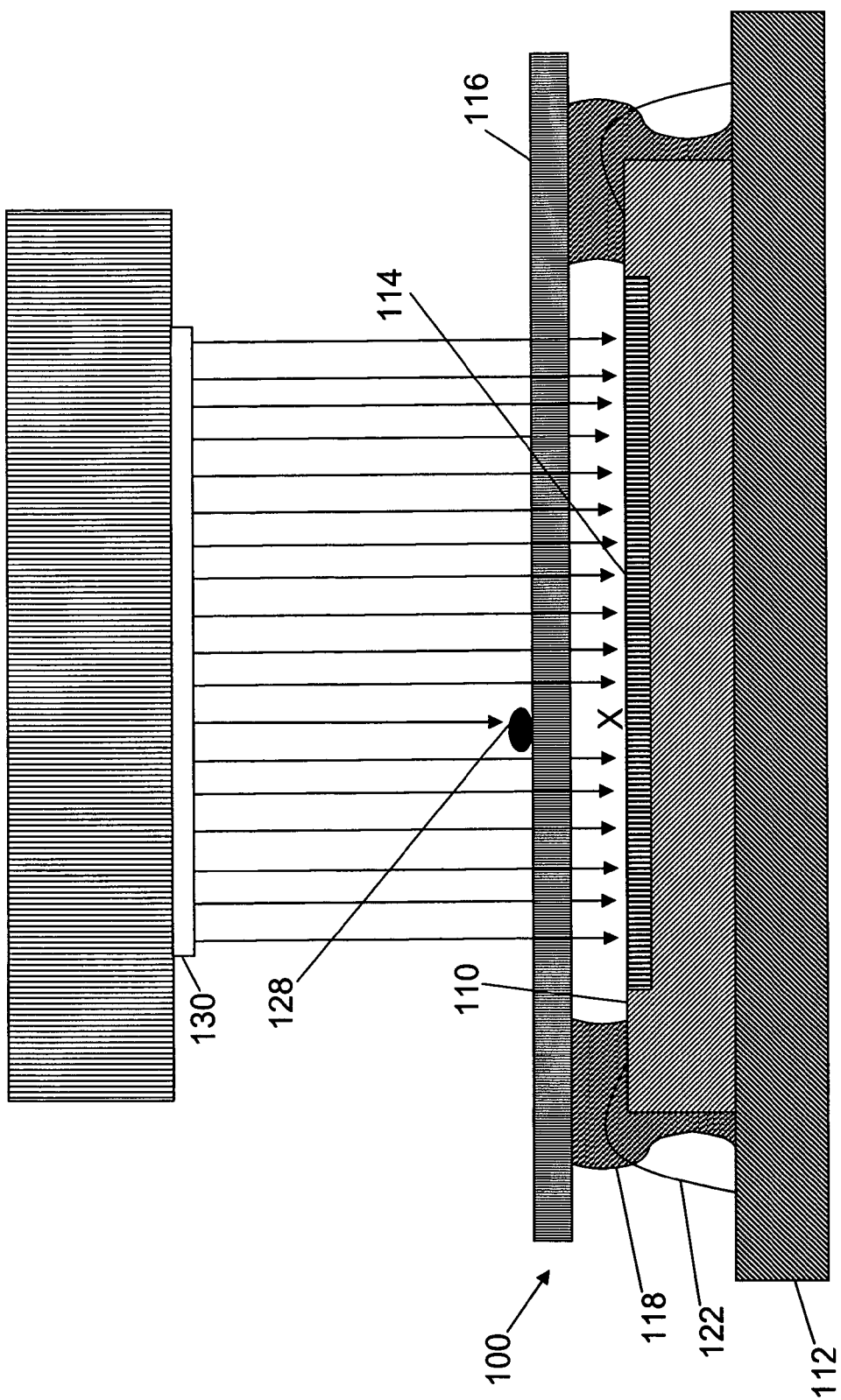
FIG. 5 illustrates a related apparatus for testing the quality of an imager die package.

By using at least two different angles at which the pixel arrays 114, 150 (FIGS. 7–11) are exposed to the light source 130, a determination can be made as to the level at which the defect is present. For example, an operator or program can determine that the package 100 (FIGS. 7 and 8) contains a particle 128 (FIGS. 7 and 8) if two separate defects, e.g. defect 124a, 124b (FIG. 9), are detected. Similarly, an operator or program can determine that the package 144 (FIGS. 10 and 11) contains a non-functional pixel (e.g., non-functional pixel 126 (FIG. 4)), if only one defect, e.g., defect 230 (FIG. 12), is detected.

The method of exposing the pixel array 114 to a light source 130 at different angles improves yields and lowers manufacturing costs by not discarding dies having fully functional pixel arrays 114 (FIG. 7), which have been obstructed by a particle 128 (FIG. 7). These particles 128 (FIG. 7) can be removed from the transparent element 116 (FIG. 7). Oftentimes, the particle 128 (FIG. 7) can be removed by blowers that push air along the surface 116a (FIG. 7) of the transparent element 116 (FIG. 7). The fully functional pixel array 114 (FIG. 7) will not be accidentally discarded, thereby increasing yield, and lowering manufacturing costs.

Figure 13:
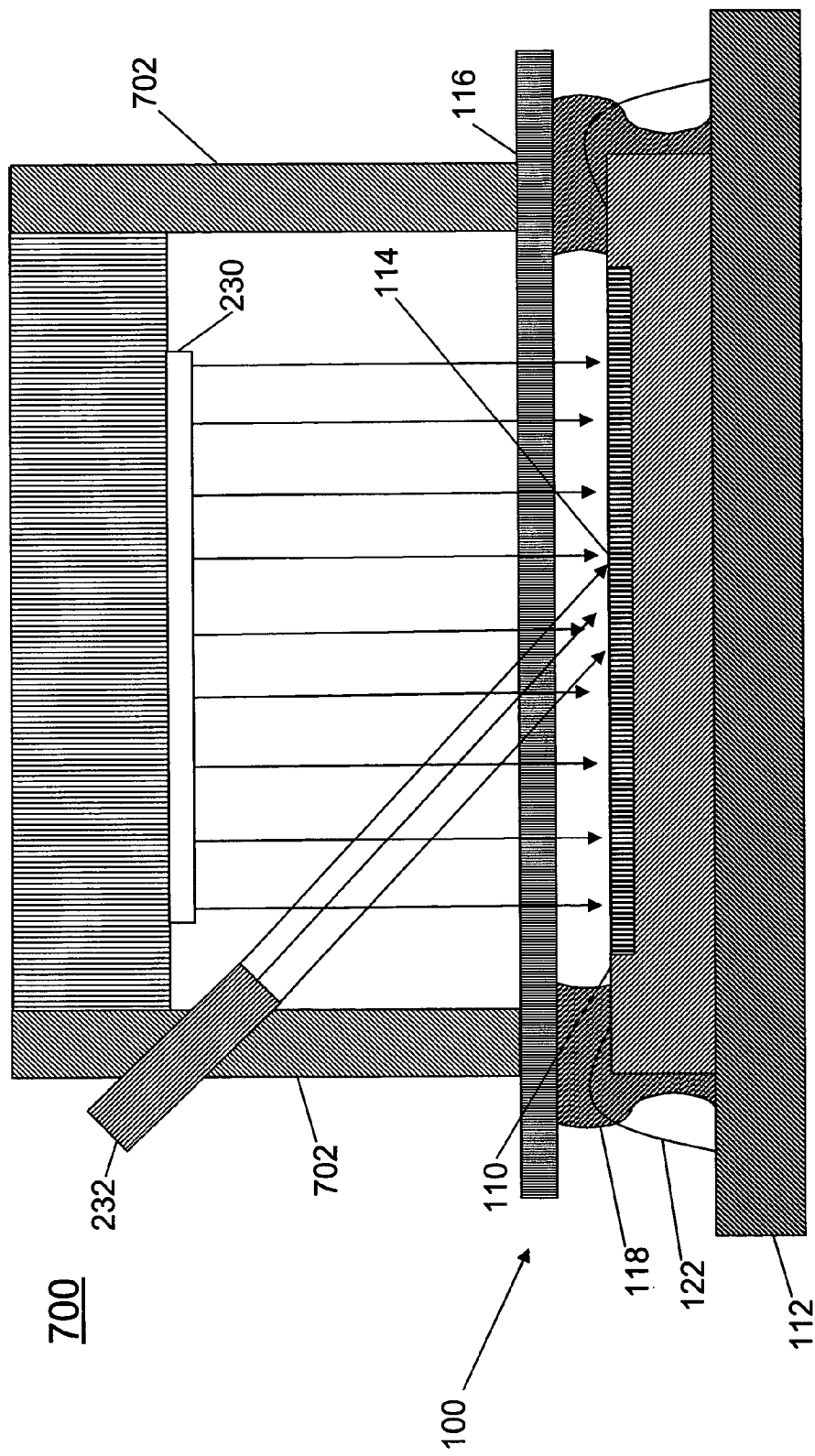
FIG. 13 illustrates an apparatus for testing the quality of an imager die package in accordance with a second exemplary embodiment of the invention.
Figure 14:
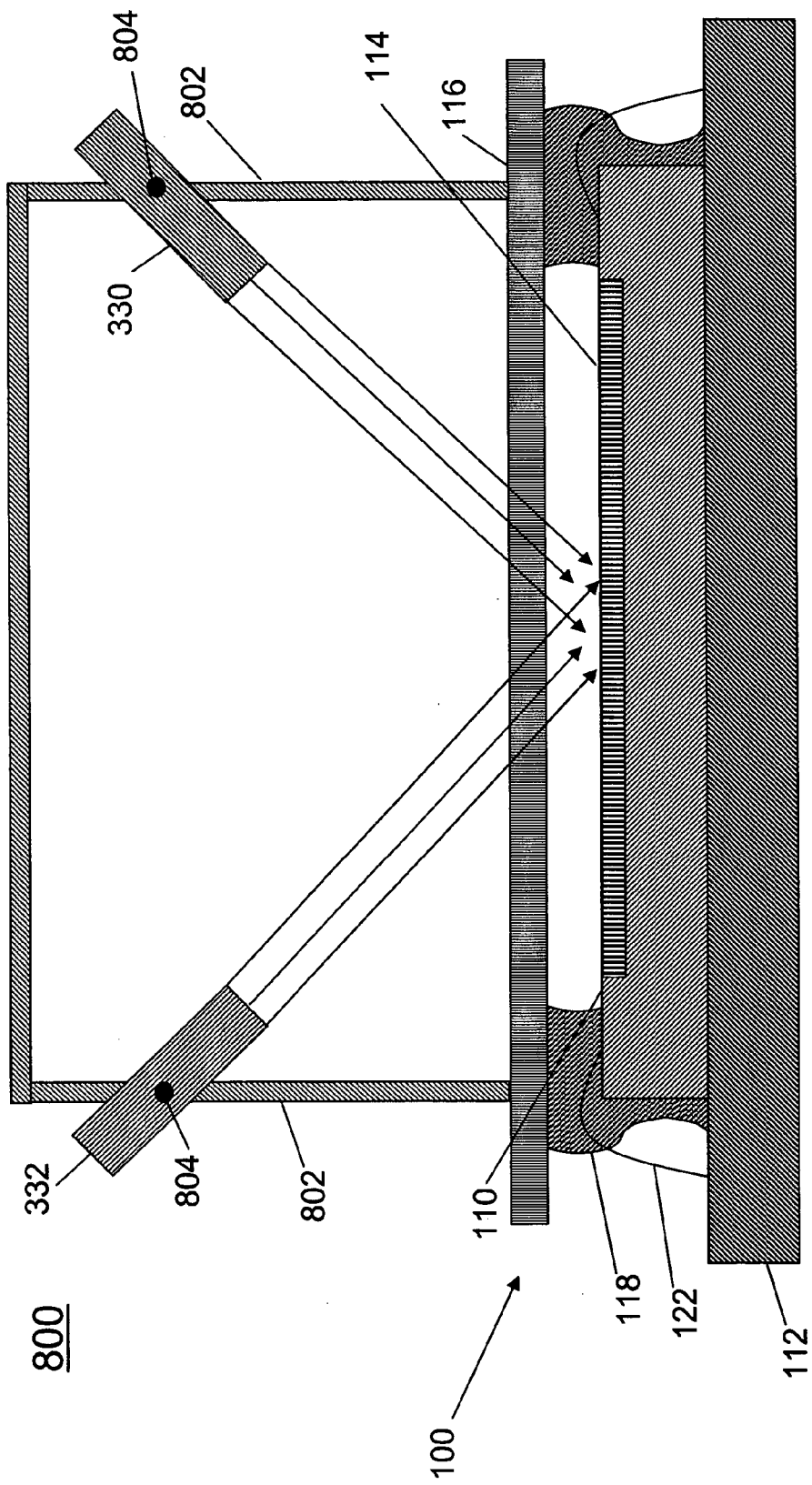
FIG. 14 illustrates an apparatus for testing the quality of an imager die package in accordance with a third exemplary embodiment of the invention.

FIGS. 13 and 14 illustrate an apparatus 700 according to a second exemplary embodiment of the invention and a second embodiment of a method of operation. During operation, the illustrated imager die package 100 is positioned under the apparatus 700, which contains two separate light sources (a first light source 230 and a second light source 232). Although the first light source 230 is illustrated as being at a 90° angle to the surface 116a of the transparent element 116, it is not intended to be limiting in any way. For example, the first light source 230 could be at an angle less than or greater than 90°, depending on the desired application.

In the illustrated embodiment, the first and second light sources 230, 232 are shown as integrated light sources on a structure having two posts 702. The posts 702 could be included on all four sides of the apparatus 700, and, together with the first light source 230, comprise an enclosed structure, thereby eliminating any contaminant light from sources other than the first and second light sources 230, 232. The elimination of contaminant light ensures that the pixel readings are not influenced by light other than the light generated within the apparatus 700, i.e., light generated by the first and second light sources 230, 232.

It should be noted that the FIG. 13 apparatus 700 is not intended to be limiting in any way. For example, in certain applications, such as "bleaching" of the pixel array 114, it is not necessary to eliminate external light sources. Bleaching refers to exposing the pixel array 114 to white light, thereby displaying a solid white image on a computer screen. Bleaching can be used with color pixel arrays, but are primarily used with black and white pixel arrays. Because certain applications do not require the elimination of external light sources, apparatus 700 could have different configurations, as described in greater detail below.

The FIG. 13 apparatus operates similarly to the FIG. 6 apparatus 600, with the exception that two light sources 230, 232 are provided rather than one (e.g., light source 130 (FIG. 6)). The imager die package 100 may be positioned beneath the apparatus 700 by a conveyor belt or some other device that can position the imager die package 100 under the apparatus 700 automatically. The pixel array 114 is exposed to light from the two light sources 230, 232 at different angles, and readings are taken to form a display image, similar to the display images 900, 1200 discussed above with respect to FIGS. 7–12.

By having two separate light sources 230, 232, the apparatus 700 can be operated by exposing the pixel array 114 of the imager die package 100 to light from the two light sources 230, 232 by a number of methods: specifically, the two light sources 230, 232 could be turned on sequentially, i.e., one after the other; overlapping, e.g., exposing the pixel array 114 to light from the first light source 230, and subsequently exposing the pixel array 114 to light from the second light source 232, while the pixel array 114 is exposed to light from the first light source 230; or simultaneously, i.e., at the same time.

Figure 3:
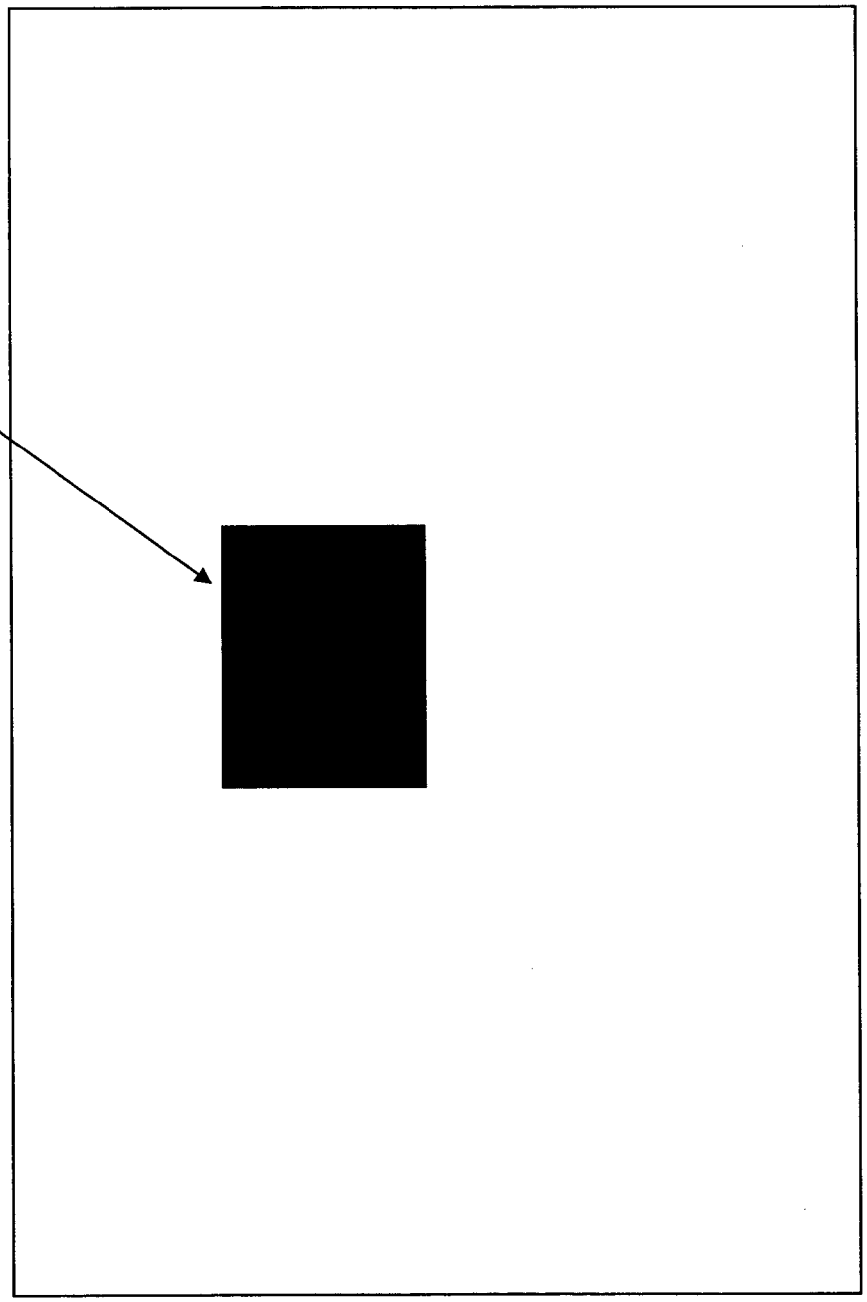
FIG. 3 illustrates a display image.

During sequential operation of the apparatus 700, the exposure of the pixel array 114 to light from the second light source 232 could be avoided if it is determined that there are no defects 124 (e.g., FIG. 3) when the pixel array 114 is exposed to light from the first light source 230. The fully functional pixel array 114 would not have to be tested further. On the other hand, if a defect 124 (e.g., FIG. 3) is detected after exposing the pixel array 114 to light from the first light source 230, the second light source 232 can emit light, and two separate display images could be generated. The two separate display images could be compared by an operator, the image processor 111 (FIG. 1), or a processor-based system, and the determination can be made as to the level at which the defect lies (i.e., the transparent element 116 or the pixel array 114).

Alternatively, the images captured by the two exposures could be simultaneously displayed as one display image. An operator, the image processor 111 (FIG. 1), or a processor-based system could determine if the defects are in the same location or in different locations. The level at which the defect is present (i.e., whether the defect is located at the transparent element 116, or the pixel array 114) can be determined by this comparison.

In a third apparatus and method of embodiment, illustrated in FIG. 14, an apparatus 800 has first and second light sources 330, 332 that are suspended from adjustable posts 802. The adjustable posts 802 can be raised and lowered depending on the desired application. Additionally, the illustrated first and second light sources 330, 332 are each rotatable about an axis 804. By being rotatable, the angle at which the light sources 330, 332 emit light can be varied during testing, similar to the FIG. 6 apparatus 600. The FIG. 14 configuration allows the apparatus 800 to use the light sources 330, 332 at different angles, thereby ensuring that any particles (e.g., particle 128 (FIG. 7)) on the transparent element 116 are recognized.

It should be noted that the posts 802 could be suspended from a suspension structure, and do not necessarily have to be touching the imager die package 100 being tested. The posts 802 could be a wire, or some other structure, and are not limited to the FIG. 14 configuration. It should also be noted that the imager die package 100 could be exposed to light sources 330, 332 either sequentially, simultaneously, or overlapping, as discussed above with respect to FIG. 13.

Although the invention was described as having light sources 130, 230, 232, 330, 332 (FIGS. 7–14) positioned above the imager die packages 100, 144 (FIGS. 6–14) being tested, it should be noted that the imager die packages 100, 144 (FIGS. 6–14) tested can be facing downward, i.e., having the transparent element 116 (e.g., FIG. 6) facing downward, and exposing the imager die packages 100, 144 (FIGS. 6–14) tested from light sources 130, 230, 232, 330, 332 (FIGS. 7–14) that are positioned below the imager die packages 100, 144 (FIGS. 6–14).

Although the various embodiments of the methods of detecting a defect have been discussed with exposing the pixel arrays, e.g., pixel array 114 (FIG. 6) with light at two different angles, it should be recognized that the method may include exposing the pixel arrays with light at several different angles. For example, pixel array 114 (FIG. 6) could be exposed to light source 130 (FIG. 6) at a third angle. Similarly, apparatus embodiments 600, 700, 800 (FIGS. 7–14) have been illustrated as having one or two light sources. It should be noted that this is not intended to be limiting in any way, and additional light sources may be included in apparatus embodiments 600, 700, 800 (FIGS. 7–14). For example, the apparatuses 700 (FIG. 13) could have a third light source at a third angle.

It should also be noted that the light sources could comprise of any light bulb or light emitting source, such as a laser or a light emitting diode. The light emitting diode could be used with a fiber optic cable.

It should also be noted that the light sources 130, 230, 232, 330, 332 (FIGS. 7–14) could use white light, monochromatic lights, or light with different wavelengths, depending on the desired application. For example, the light sources could have three different light emitting diodes each; a red, blue, and green light emitting diode for each light source. The light sources 130, 230, 232, 330, 332 (FIGS. 7–14) could test color pixel arrays three separate times. The first test would test all of the blue pixels in the pixel array by emitting only blue light, the second test would test all of the green pixels in the pixel array by emitting only green light, and the final test would test all of the red pixels in the pixel array by emitting only red light. During operation of the apparatus embodiments 600, 700, 800 (FIGS. 7–14), the light sources 130, 230, 232, 330, 332 (FIGS. 7–14) having a plurality of light emitting diodes could be operated sequentially, simultaneously, or in an overlapping manner, as described above with respect to FIG. 13.

It should also be noted that the stored electrical signals need not be processed to output display images 900, 1200 (FIGS. 9 and 12). For example, a program can determine whether defects (e.g., defects 124a, 124b (FIGS. 7 and 8)) are present within the electrical signals themselves. Therefore, display images are not necessarily required, but have been discussed above with respect to FIGS. 7–14 for illustrative purposes.

Figure 15:
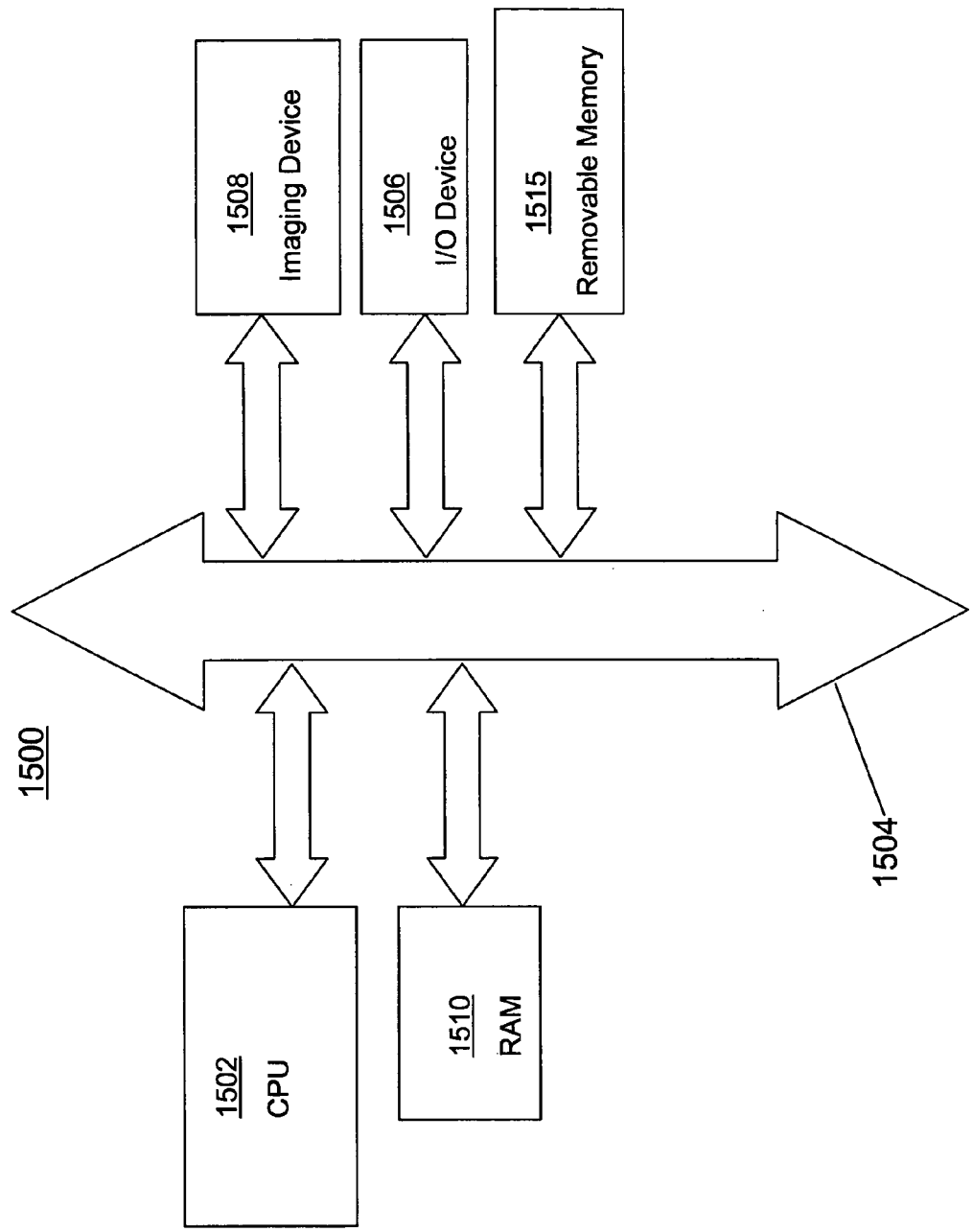
FIG. 15 is a block diagram of a processor-based system constructed in accordance with an exemplary embodiment of the invention.

FIG. 15 illustrates a processor-based system 1500 that may be used to test the imager die package 100 (e.g., FIG. 6) in conjunction with one of the exemplary apparatus embodiments 600, 700, 800 (FIGS. 6–14) of the invention. The processor-based system 1500 could be programmed to operate the illustrated embodiments 600, 700, 800 (FIGS. 6–14), and could be used to determine whether any defects are present in a die. The processor-based system includes an imaging device 1508 being tested. The imaging device 1508 could be the imager die package 100 (e.g., FIG. 6) itself, or a device including the imager die package 100 (e.g., FIG. 6). Without being limiting, the imaging device 1508 may include a computer system, camera system, scanner, machine vision, vehicle navigation, video phone, surveillance system, auto focus system, star tracker system, motion detection system, image stabilization system, medical device, and data compression system.

The processor-based system 1500 generally comprises a central processing unit (CPU) 1502, such as a microprocessor, that communicates with an input/output (I/O) device 1506 over a bus 1504. Imaging device 1508 also communicates with the CPU 1502 over the bus 1504, and may include the imager die 110 discussed above with respect to FIG. 1. The processor-based system 1500 also includes random access memory (RAM) 1510, and can include removable memory 1515, such as flash memory, which also communicates with CPU 1502 over the bus 1504. Imaging device 1508 may be combined with a processor, such as a CPU, digital signal processor, or microprocessor, with or without memory storage on a single integrated circuit or on a different chip than the processor, as discussed above with respect to FIG. 1.

Any of the memory storage devices in the processor-based system 1500 could include a program capable of employing the above-described features, e.g., moving the light sources 130, 230, 232, 330, 332 (FIGS. 7–14), comparing sequential display images, and determining the level at which a defect is located. The processor for producing an output image in accordance with the processes described and illustrated with reference to FIGS. 6–14 may be conducted by the imager processor 111 (FIG. 1) within imaging device 1508 or by the CPU 1502, or by yet another processor communicating with system 1500.

The above description and drawings illustrate exemplary embodiments which achieve the objects, features, and advantages of the present invention. Although certain advantages and exemplary embodiments have been described above, those skilled in the art will recognize that substitutions, additions, deletions, modifications, and/or other changes may be made without departing from the spirit or scope of the invention. Accordingly, the invention is not limited by the foregoing description but is only limited by the scope of the appended claims.

What is claimed as new and desired to be protected by Letters Patent of the United States is:

1. A method of detecting a defect in an imager die package, said method comprising the acts of:
    exposing the imager die package to light at a first angle relative to a surface of said imager die package;
    exposing said imager die package to light at a second angle, said first and second angles being different from each other;
    outputting electrical signals from the imager die package based on said exposures to light; and
    determining a level of said imager die package at which a defect is present based on the output electrical signals.

2. The method of claim 1, wherein the electrical signals are further processed to generate a display image.

3. The method of claim 2, wherein the display image comprises a combination of a first display image based on said exposure to light at the first angle and a second display image based on the exposure to light at the second angle.

4. The method of claim 1, wherein said first angle is perpendicular to said surface of the imager die package.

5. The method of claim 1, further comprising the act of exposing the imager die package to light at a third angle, the third angle being different than said first and second angles.

6. The method of claim 1, wherein said determining step detects a defective pixel.

7. The method of claim 1, wherein said determining step detects a particle obstructing pixels.

8. The method of claim 1, wherein said exposing steps occur sequentially.

9. The method of claim 1, wherein said exposing steps occur simultaneously.

10. The method of claim 1, wherein said exposing steps occur in an overlapping manner.

11. A method of testing an imager, said method comprising the acts of:
    exposing a pixel array of the imager to light from a first light source at a first angle relative to a surface of the imager,
    exposing said pixel array to light from a second light source at a second angle, the second angle being different from the first angle;
    outputting electrical signals from the imager based on said exposures to light; and
    determining a level of said imager die package at which a defect is present based on the output electrical signals.

12. The method of claim 11, wherein said exposing steps occur sequentially.

13. The method of claim 11, wherein said exposing steps occur simultaneously.

14. The method of claim 11, wherein said exposing steps occur in an overlapping manner.

15. The method of claim 11, wherein said electrical signals are further processed to generate a display image.

16. An imager die package testing apparatus, said apparatus comprising:
    a first light source positioned over the imager die package at a first angle relative to a surface of an imager of the imager die package;
    a second light source positioned over the imager die package at a second angle, said first and second angles being different from each other; and
    a processor for determining a level of said imager die package at which a defect is present based on output electrical signals from the imager.

17. The apparatus according to claim 16, wherein said first and second light sources are integrated in a structure having posts.

18. The apparatus according to claim 17, wherein said posts are adjustable.

19. The apparatus according to claim 17, wherein said structure is enclosed.

20. The apparatus according to claim 16, wherein at least one of said first and second light sources is rotatable about an axis.

21. The apparatus according to claim 20, wherein said first and second light sources are suspended from a wire.

22. The apparatus according to claim 16, wherein said first angle is perpendicular to a surface of said imager die package.

23. The apparatus according to claim 16, further comprising a third light source at a third angle, said third angle being different than said first and second angles.

24. The apparatus according to claim 16, wherein one of said first and second light sources is a light emitting diode.

25. The apparatus according to claim 16, wherein one of said first and second light sources has a plurality of light emitting diodes.

26. The apparatus according to claim 25, wherein said light emitting diodes are selected from the group comprising blue, red, and green.

27. The apparatus according to claim 16, wherein one of said first and second light sources emits a white light.

28. The apparatus according to claim 16, wherein one of said first and second light sources emits a monochromatic light.

29. The apparatus according to claim 16, wherein said processor detects a defective pixel.

30. The apparatus according to claim 16, wherein said processor detects a particle obstructing pixels.

31. An imager die package testing apparatus, comprising:
a light source suspended from a structure and being rotatable about an axis such that said light source can be positioned over the imager die package at first and second angles relative to a surface of the imager die package; and
a processor for storing information from a pixel array of the die package; said processor determining a level of said imager die package at which a defect is present.

32. The apparatus according to claim 31, wherein said processor detects a defective pixel.

33. The apparatus according to claim 31, wherein said processor detects a particle obstructing pixels.

34. The apparatus according to claim 31, wherein said light source has a plurality of light emitting diodes.

35. The apparatus according to claim 34, wherein said light emitting diodes are selected from the group comprising blue, red, and green.

36. The apparatus according to claim 31, wherein said processor includes a program, said program causing the processor to execute the following steps:
positioning said light source over the imager die package having said pixel array to the first angle;
exposing said pixel array to light from the light source;
storing information from the pixel array in said processor;
positioning said light source over said pixel array to the second angle, said second angle being different from said first angle;
exposing said pixel array to light from the light source;
storing information from said pixel array in said processor;
outputting electrical signals based on said stored information; and
determining the level at which any defects in said imager die package is located based on said electrical signals.

37. An imager testing device, said imager testing device comprising:
means for shining light on an imager in an imager die package at a first angle and a second angle, said first and second angles being different from each other; and
determining means for determining a level at which a defect in the package is present from the light shone on the package at the angles and detected by the imager.

38. The device of claim 37, wherein said means for shining light on a package comprises one light source.

39. The device of claim 38, wherein said light source has a plurality of light emitting diodes.

40. The device of claim 39, wherein said light emitting diodes are selected from the group comprising blue, red, and green.

41. The device of claim 37, wherein said means for shining light on a package comprises at least two light sources.

42. The device of claim 37, wherein said determining means comprises a processor.

43. The device of claim 37, wherein said determining means detects a defective pixel.

44. The device of claim 37, wherein said determining means detects a particle obstructing pixels.

45. An imager testing apparatus, comprising:
a transparent layer for passing received light to an imager having a pixel array;
a movable light source that can be positioned relative to the transparent layer and imager at first and second angles; and
a processor having memory for storing information from said pixel array of the imager based on images captured when said light source is at said first and second angles, said processor being capable of determining a defect at either of said transparent layer and said imager.

46. The imager testing apparatus according to claim 45, wherein said processor detects a defective pixel of said imager.

47. The imager testing apparatus according to claim 45, wherein said processor detects a particle obstructing light from reaching said imager.

48. The imager testing apparatus according to claim 45, wherein said light source comprises a plurality of light emitting diodes.

49. The imager testing apparatus according to claim 48, wherein said plurality of light emitting diodes comprises at least one of blue, red, and green light emitting diodes.

50. A procedure for light testing an imager, comprising:
transmitting light through at least one transparent layer to said imager from two different angles, said imager having a sensor capable of sensing said transmitted light; and
analyzing the resulting images sensed by said sensor to determine whether a defect is present at the sensor or at the transparent layer.

* * * * *